(12) United States Patent
Favero et al.

(10) Patent No.: US 11,280,735 B2
(45) Date of Patent: Mar. 22, 2022

(54) METHOD FOR DETERMINING THE ANIONIC CHARGE DENSITY OF A POLYMER

(71) Applicant: SPCM SA, Andrezieux Boutheon (FR)

(72) Inventors: Cédrick Favero, Andrezieux Boutheon (FR); Olivier Braun, Andrezieux Boutheon (FR); Renaud Souzy, Andrezieux Boutheon (FR); Arthur Marais, Lochrist (FR); Thomas Brichart, Lyons (FR)

(73) Assignee: SPCM SA, Andrezieux Boutheon (FR)

( * ) Notice: Subject to any disclaimer, the term of this patent is extended or adjusted under 35 U.S.C. 154(b) by 338 days.

(21) Appl. No.: 16/477,058

(22) PCT Filed: Dec. 15, 2017

(86) PCT No.: PCT/FR2017/053624
§ 371 (c)(1),
(2) Date: Jul. 10, 2019

(87) PCT Pub. No.: WO2018/142034
PCT Pub. Date: Aug. 9, 2018

(65) Prior Publication Data
US 2021/0285876 A1 Sep. 16, 2021

(30) Foreign Application Priority Data
Jan. 31, 2017 (FR) ...................................... 1750814

(51) Int. Cl.
*G01N 21/64* (2006.01)
*G01N 33/28* (2006.01)

(52) U.S. Cl.
CPC ....... *G01N 21/6408* (2013.01); *G01N 21/643* (2013.01); *G01N 33/2835* (2013.01)

(58) Field of Classification Search
CPC ............ G01N 21/6408; G01N 21/643; G01N 33/2835
See application file for complete search history.

(56) References Cited

U.S. PATENT DOCUMENTS 7,700,702 B2 4/2010 Gaillard et al.
2016/0290923 A1* 10/2016 Nuutinen ............... G01N 21/77

FOREIGN PATENT DOCUMENTS

FR 2868783 A1 10/2005
WO 2004/021004 A1 3/2004
(Continued)

OTHER PUBLICATIONS

Smith-Palmer, et al., "Determination of the charge density of acrylamide/acrylate copolymers by tensammetry", Jan. 1990, Can. J. Chem., 68,26. (Year: 1990).*

(Continued)

*Primary Examiner* — Samuel P Siefke
*Assistant Examiner* — Henry H Nguyen
(74) *Attorney, Agent, or Firm* — Heslin Rothenberg Farley & Mesiti P.C.

(57) ABSTRACT

The present invention relates to a method for determining the anionic charge density of at least one polymer present in a sample, according to the following steps:
  bringing the at least one polymer present in the sample into contact with, and enabling the interaction thereof with, a developer solution comprising lanthanide (III) ions,
  exciting the sample at an excitation wavelength $\lambda_{exc}$ and detecting, by time-resolved photoluminescence, a signal originating from the lanthanide (III) ions that have interacted with the at least one polymer at an emission wavelength $\lambda_{em}$, and
(Continued)

determining the anionic charge density of the at least one polymer of the sample using the signal detected at the emission wavelength $\lambda_{em}$.

20 Claims, 5 Drawing Sheets

(56) References Cited

FOREIGN PATENT DOCUMENTS

WO     2015/075299 A1    5/2015
WO     2016/203119 A1    12/2016

OTHER PUBLICATIONS

International Search Report (and English translation) and Written Opinion of the International Searching Authority for PCT/FR2017/053624 dated Mar. 27, 2018.

Gudgin Dickson, E.F., et al., "Ultrasensitive Bioanalytical Assays Using Time-Resolved Fluorescence Detection", Pharmac. Ther., vol. 66, pp. 207-235 (1995).

* cited by examiner

METHOD FOR DETERMINING THE ANIONIC CHARGE DENSITY OF A POLYMER

CROSS REFERENCE TO RELATED APPLICATIONS

This application is a national stage filing under section 371 of International Application No. PCT/FR2017/053624, filed on Dec. 15, 2017, and published on Aug. 9, 2018 as WO 2018/142034, which claims priority to French Application No. 1750814, filed on Jan. 31, 2017. The entire contents of WO 2018/142034 are hereby incorporated herein by reference.

FIELD OF THE INVENTION

The present invention relates to a method for determining the anionic charge density of polymer(s). More precisely, the present invention relates to a method for determining the anionic charge density of polymer(s) present in a sample using time-resolved photoluminescence.

DESCRIPTION OF THE PRIOR ART

Anionic polymers are used in a variety of fields such as water treatment, sludge treatment, and enhanced oil and gas recovery. In these various fields, it is important to know the characteristics of polymers and in particular their anionic charge density. For example, in the field of enhanced oil recovery, polymers are degraded by the effects of pressure, temperature, and the chemical environment within the underground formation. At the well outlet, the anionic charge density of the polymer is unknown due to these degradations.

A variety of analytical techniques are currently used to determine the anionic charge density of polymers. Examples of techniques include conductivity titration, nitrogen content, potentiometric titration, $^{13}C$ NMR spectroscopy, infrared spectroscopy, UV spectroscopy, thermogravimetric analysis, and calorimetry.

However, these methods are quite limiting because, for the most part, a relatively pure sample is essential, which requires complex purification steps. In addition, these methods require knowing the polymer concentration of the sample, a characteristic that is not always known, is difficult to measure, and is often dependent on the anionic charge density.

Therefore, there is a need for a simple and practical method for determining the anionic charge density of polymers in a sample without knowing the polymer(s) concentration.

DISCLOSURE OF THE INVENTION

The purpose of this invention is a method for determining the anionic charge density of at least one polymer present in a sample. This method comprises the following steps:
optionally, pre-treating the sample,
bringing the at least one polymer present in the sample into contact with, and enabling its interaction with, a developer solution comprising lanthanide (III) ions,
exciting the sample at an excitation wavelength of $\lambda_{exc}$ and detecting, by time-resolved photoluminescence, a signal originating from the lanthanide (III) ions that have interacted with the at least one polymer at an emission wavelength $\lambda_{em}$, and
determining the anionic charge density of the at least one polymer in the sample using the signal detected at the emission wavelength $\lambda_{em}$.

The method of this invention may be used to determine the anionic charge density of polymers present in samples from underground formations such as oil or gas wells; water or sludge treatment processes; cosmetics; detergents; paper manufacturing; and or mining industry. Preferably, the method of this invention is used to determine the anionic charge density of polymers present in samples from underground formations, in particular oil or gas wells. Samples are advantageously taken from a production well, particularly production water coming from an oil or gas recovery process. The determination of anionic charge density provides information on the degradation that polymers are subjected to in the underground formation. In addition, if the production water is reinjected, it is important to know the anionic charge density in order to optimally readjust the anionic charge density of the solution.

It was discovered in a totally surprising manner that by using the method of the invention, the signal obtained by time-resolved photoluminescence from the product of the interaction between the polymers and the developer solution comprising the lanthanide ions, precisely correlates with the anionic charge density of the polymers present in a sample.

According to the invention, the time-resolved photoluminescence measurement that is preferably used is the time-resolved fluorescence measurement.

This method has the advantage of being completely independent of the molecular weight of the polymers. Thus, this method is perfectly suitable for polymers with a molecular weight between 1000 g/mol and 35 million g/mol. Unless otherwise specified, the "molecular weight" of a polymer refers to the weight average molecular weight.

According to the invention, the polymer may be a natural polymer from the polysaccharide group such as starch, guar, cellulose, dextran, or xanthan. According to the invention, the polymer may also be a polycondensate. Advantageously, the sample comprises at least one polymer having one or more anionic charge(s). Advantageously, all polymers in the sample include one or more anionic charge(s).

The polymer can be a copolymer made of at least two or more monomers.

According to the invention, the polymer may have a linear, branched, cross-linked, star-shaped or comb-shaped structure.

According to the invention, the polymer can be obtained by copolymerization of at least one anionic monomer and at least one non-ionic monomer (A) and optionally at least one cationic or zwitterionic monomer.

The anionic monomer(s) can be chosen from a large group. Advantageously it is a water-soluble monomer, i.e., a monomer soluble in water under conventional polymerization conditions. These monomers may have acrylic, vinyl, maleic, fumaric, malonic, itaconic, or allylic functions. They may contain a carboxylate, phosphonate, phosphate, sulfate, sulfonate, or another anionically charged group. The anionic monomer may be in the form of an acid or in the form of an alkaline earth metal or alkali metal salt. Examples of suitable monomers include acrylic acid; methacrylic acid; itaconic acid; crotonic acid; maleic acid; fumaric acid; monomers of the strong acid type having for example a function of the sulfonic acid or phosphoric acid type, such as 2-acrylamido-2-methylpropane sulfonic acid, vinylsulfonic acid, vinylphosphonic acid, allylsulfonic acid, allylphosphonic acid, or styrenesulfonic acid; and the water-soluble alkali metal, alkaline earth metal, or ammonium salts thereof.

According to a particular embodiment, the polymer advantageously comprises between 1 and 99 mol % of anionic monomer(s), preferably between 3 and 80 mol % and more preferably between 5 and 50 mol %, relative to the total number of moles of monomers.

The monomer (A) may be a non-ionic monomer that notably can be selected from the group comprising water-soluble vinyl monomers, and particularly acrylamide; methacrylamide; N-isopropylacrylamide; N,N-dimethylacrylamide; N-vinylformamide; acryloyl morpholine; N,N-diethyl acrylamide; N-tert-butyl acrylamide; N-tert-octylacrylamide; N-vinylpyrrolidone; N-vinylcaprolactam; N-vinyl-imidazole; and diacetone acrylamide.

The non-ionic monomer can also be chosen from monomers with formula:

D-Z-D' where:
D is a polymerizable unsaturated chemical function of the acrylate, methacrylate, acrylamido, methacrylamido, vinylic or allylic type;
D' represents hydrogen or an alkyl group (preferably $C_1$-$C_{22}$) or an aryl group (preferably $C_1$-$C_{22}$);
Z has the following structure: —(OE)w-(OP)x-(OBu)z-
where:
OE, OP, OBu refer respectively to ethylene oxide (—$CH_2$—$CH_2$—O—), propylene oxide (—$CH_2$—$CH_2$—$CH_2$—O—), and butylene oxide (—$CH_2$—$CH_2$—$CH_2$—$CH_2$—O—).
The arrangement between the various OE and/or OP and/or OBu units can be statistical, alternating, gradient, or block.
w, x and z are integers between 0 and 150 and w+x+z≠0.

According to a particular embodiment, the polymer advantageously comprises between 1 and 99.9 mol % of non-ionic monomer(s), preferably between and 95 mol % and more preferably between 60 and 90 mol %, relative to the total number of moles of monomers.

The cationic monomer may be of the acrylamide, acrylic, vinylic, allylic or maleic type having an quaternary amine or ammonium function. Mention may be made, in particular and in a non-limiting way, of quaternized or salified dimethylaminoethyl acrylate (ADAME), and dimethylaminoethyl methacrylate (MADAME), dimethyldiallylammonium chloride (DADMAC), acrylamido propyltrimethyl ammonium chloride (APTAC) and methacrylamido propyltrimethyl ammonium chloride (MAPTAC). The cationic monomers derived from acrylamide and carrying a hydrophobic chain described in document FR 2 868 783 may be used.

According to a particular embodiment, the polymer advantageously comprises between 1 and 30 mol % of cationic monomer(s), preferably between 2 and mol %, and more preferably between 5 and 15 mol %, relative to the total number of moles of monomers.

According to the invention, the developer solution includes lanthanide (III) ions. The lanthanide (III) ions are advantageously chosen from europium, terbium, samarium or dysprosium ions. Preferably the lanthanide (III) ions are europium or terbium ions. In the developer solution, the lanthanide (III) can be a lanthanide salt, for example a lanthanide halide such as europium chloride.

According to a particular embodiment, the developer solution may comprise one or more buffer solutions to improve the signal-to-noise ratio of the samples analyzed. Examples of buffers that can be used include sulfonic acid derivatives, such as for example HEPES (2-[4-(2-hydroxyethyl) piperazin-1-yl]ethanesulfonic acid, pKa 7.48), PIPES (1,4-piperazinediethanesulfonic acid, pKa 6.76), MOPS (3-morpholinopropane-1-sulfonic acid, pKa 7.2) and MES (2-(N-morpholino)ethanesulfonic acid, pKa 6.15). Preferably the buffer is HEPES. Developer solutions that can be used include those sold by the Glincs company.

The developer solution is advantageously an aqueous solution.

According to another particular embodiment of the invention, one or more buffers, mentioned above, can be added to the sample before signal detection at the emission wavelength $\lambda_{em}$, in order to improve the signal-to-noise ratio and the signal-to-background noise ratio of the signals from the detected samples.

The quantity of lanthanide (III) ions added to the sample is advantageously between 1 ppm and 10,000 ppm, preferably between 5 ppm and 1000 ppm. The amount of lanthanide (III) ions is expressed in weight relative to the weight of the sample before the sample comes into contact with the developer solution.

According to the invention, the density of anionic charges is quantified using a time-resolved photoluminescence method that is notably described in the article "*Ultrasensitive bioanalytical assays using time resolved fluorescence detection*", Pharmacol. Ther., Vol. 66(2), pages 207-35, 1995. This is based on the application of a time delay, known as the integration time, between the excitation of the sample to be analyzed and the measurement of the signal emitted, in order to avoid short-lifetime parasitic photoluminescences. This method can be used at room temperature, notably with a device like the Cary Eclipse from Agilent Company.

The wavelength used in the invention can be selected or determined by studying the maximum excitation in the excitation spectrum of the product of the interaction between the polymers and the developer solution comprising lanthanide (III) ions. For example, the excitation wavelength $\lambda_{exc}$ can be between 200 nm and 600 nm and the emission signal wavelength $\lambda_{em}$ can be between 300 nm and 800 nm.

The integration time can be between 0.001 ms and 10 ms (ms=milliseconds), preferably between 0.01 and 5 ms, and more preferably between 0.1 and 3 ms. In some cases, the longer this time, the better the signal-to-noise ratio, which improves the reliability of the measurement. The photon collection time can range from 5 to 10 ms, for example.

In one embodiment of the invention, a signal modifier comprising a cationic compound may be added to the sample before the sample is excited. The signal modifier can be used to modify the sampling signal, for example its intensity, or to modify the difference between the excitation wavelengths for the various polymers. The signal modifier can include a metal ion that is advantageously chosen from copper, nickel, chrome, iron, gold, silver, cobalt, or mixtures thereof. Preferably, the signal modifier includes copper (II). The signal modifier can include a cationic polymer of low molecular weight, advantageously less than 25,000 g/mol.

The sample can optionally be pre-treated before the anionic charge density is determined. This pre-treatment can be useful when the sample includes salts, for example inorganic salts present in production water, or insoluble particles. Production water is water recovered after water/hydrocarbon separation in an oil or gas recovery process.

In one embodiment of the invention, the sample can be purified before the addition of the developer solution comprising the lanthanide (III) ions in order to remove substances and/or compounds that interfere with the signal measured at emission wavelength $\lambda_{em}$. For example, pre-cleaning can help minimize the background noise caused by the components of the sample. Examples of purification processes that may be used in the invention include centrifugation, size-exclusion chromatography, cleaning with solid phase extraction (SPE) cartridges, dialysis techniques, extraction methods for hydrocarbon removal, filtration, microfiltration, ultrafiltration, nanofiltration, membrane centrifugation and/or other methods to separate low-molecular-weight polymeric species (advantageously less than 1000 g/mol).

In one embodiment of the invention, the salt concentration of the sample may be modified and/or the insoluble particles may be removed before adding the developer solution comprising the lanthanide (III) ions. Modifying the salt concentration of the sample may increase or decrease the salt concentration before the developer solution containing lanthanide (III) ions is added.

In a particular embodiment of the invention, if the sample is too viscous because of an initial polymer concentration that is too high, the sample can be diluted before adding the developer solution containing the lanthanide (III) ions. Diluents can be chosen from water, aqueous buffer solutions, saline solutions that may or may not be saturated in salts, or mixtures thereof. As previously indicated, the concentration of the polymer sample does not need to be known in order to determine its anionic charge density.

In a particular embodiment of the invention, one or more of the above pre-treatment steps may be performed on a sample before its anionic charge density is measured. For example, prior to measurement, the sample can be purified and/or diluted.

In a particular embodiment of the invention, the pH value of the sample is adjusted to an appropriate level. The pH of the sample is advantageously between 3 and 8, and preferably between 5 and 8. Any appropriate buffer that does not significantly interfere with the detection of the sample signal can be used. Examples of buffers are given above, but other buffers can also be used.

To determine the anionic charge density of polymers, a standard curve or standard points can be prepared before employing the determination method. The anionic charge density can be calculated from the signal by referring to the standard curve or to the predetermined standard points. Alternatively, the measuring instrument can be pre-calibrated.

The following protocol for determining the anionicity of a polymer can be followed:
1) Different sample series are prepared by successively diluting various stock solutions of polymers of known anionicity with water, having advantageously the characteristics (including salinity and conductivity) of the sample X of unknown anionicity. The samples from each series are then diluted with a lanthanide developer solution and analyzed by Time-Resolved Fluorescence (TRF). The measurement parameters as well as the emission and excitation wavelengths are adjusted according to the type of lanthanide.
2) For each series, the slopes of the TRF Signal Intensity vs. Dilution Rate curves are extrapolated and a Slope vs. Anionicity calibration curve is developed.
3) A new series of samples is then prepared by successively diluting a sample X of unknown anionicity. After TRF measurement of these samples, the slope of the TRF Signal Intensity vs Dilution Rate curve is extrapolated.
4) After the extrapolated slope in 3) is correlated with the anionicity calibration line developed in (2), the previously unknown anionicity of the sample X is deduced.

The dilution steps can be performed by adding water. However, when the sample comes from production water, all dilution steps can be performed with a brine that has the same conductivity and salinity characteristics as the production water, even for standard polymers.

As previously mentioned, the polymer concentration, even in standard polymers, does not need to be known in order to implement the invention.

The invention and the advantages deriving therefrom will be better understood from the following figures and examples provided as a non-limiting illustration of the invention.

EXAMPLE EMBODIMENTS OF THE INVENTION

The following abbreviations are used:
AANa: Sodium Acrylate
AM: Acrylamide
$\lambda_{em}$: Emission wavelength
$\lambda_{exc}$: Excitation wavelength Example 1—Determining the Anionicity of a Polymer Present in Industrial Water This example concerns the determination of the anionicity of an acrylamide/sodium acrylate polymer present in production water coming from oil production from reservoirs that use enhanced oil recovery techniques that inject a polymer-based solution.

a) Preparation of Control Solutions

The following solutions of various unknown concentrations are prepared by successively diluting a polymer stock solution with water that has the same salinity as the production water to be analyzed (Table 1).

The salinity of the production water is:

NaCl concentration: 25.00 g·L$^{-1}$
CaCl$_2$) concentration: 1 g·L$^{-1}$
A brine is prepared in such a way as to obtain the same salinity characteristics as the production water. This brine is used for diluting the various solutions.

b) Interaction with Developer Solutions

Each of the solutions listed in Table 1 is mixed with a developer solution of Terbium III Chloride sold by Glincs, using the ratio of (1 vol/10 vol). The pH is 6.5.

TABLE 1

List of dilutions of various polymer stock solutions

| Solution | Polymer Reference | Chemical composition (mol %) AANa | AM | Dilution in Production Water |
|---|---|---|---|---|
| A-1 | A | 20 | 80 | 1/10 |
| A-2 | | | | 1/20 |
| A-3 | | | | 1/50 |
| A-4 | | | | 1/100 |
| A-5 | | | | 1/150 |
| B-1 | B | 30 | 70 | 1/10 |
| B-2 | | | | 1/20 |
| B-3 | | | | 1/50 |
| B-4 | | | | 1/100 |
| B-5 | | | | 1/150 |
| C-1 | C | 40 | 60 | 1/20 |
| C-2 | | | | 1/50 |
| C-3 | | | | 1/100 |
| C-4 | | | | 1/150 |
| D-1 | D | 50 | 50 | 1/20 |
| D-2 | | | | 1/50 |
| D-3 | | | | 1/100 |
| D-4 | | | | 1/150 |
| E-1 | E | 70 | 30 | 1/10 |
| E-2 | | | | 1/20 |
| E-3 | | | | 1/50 |
| E-4 | | | | 1/100 |
| E-5 | | | | 1/150 | c) Time-Resolved Photoluminescence Measurement

Measurements are made at 20° C. in a quartz cuvette on a spectrometer like the Cary Eclipse Fluorescence Spectrophotometer from Agilent with the following characteristics:
75 kW Xenon flash lamp
Czerny-Turner monochromators
PM detector at 800 V
$\Delta_{pulse}$=2 μs
The excitation spectra of the samples are performed between 200 and 450 nm and the emission wavelength $\lambda_{em}$ is 545 nm.
The measurement parameters are set as follows:
Time: 0.1 ms
Photon collection time: 5 ms
Lamp frequency: 100 Hz
Number of flashes: 1
The analysis is started using the software controlling the spectrofluorometer.

d) Determination of Control Sample Anionicity

Figure 1:
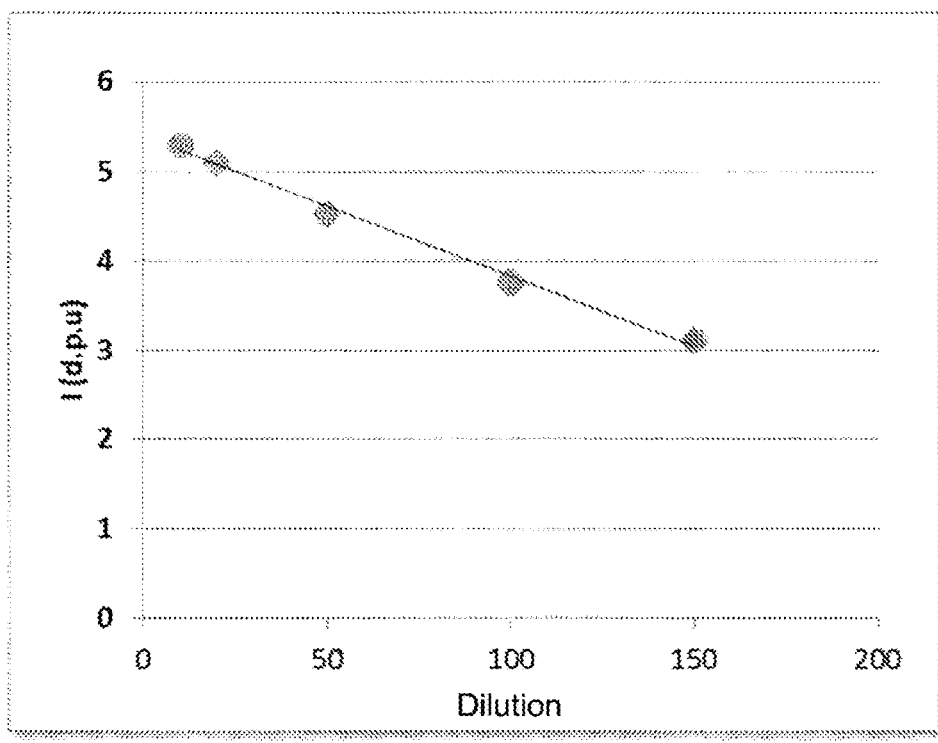
FIG. 1 shows the graph of signal intensity at the emission wavelength $\lambda_{em}$ as a function of the dilution of a stock solution of a standard polymer.
Figure 2:
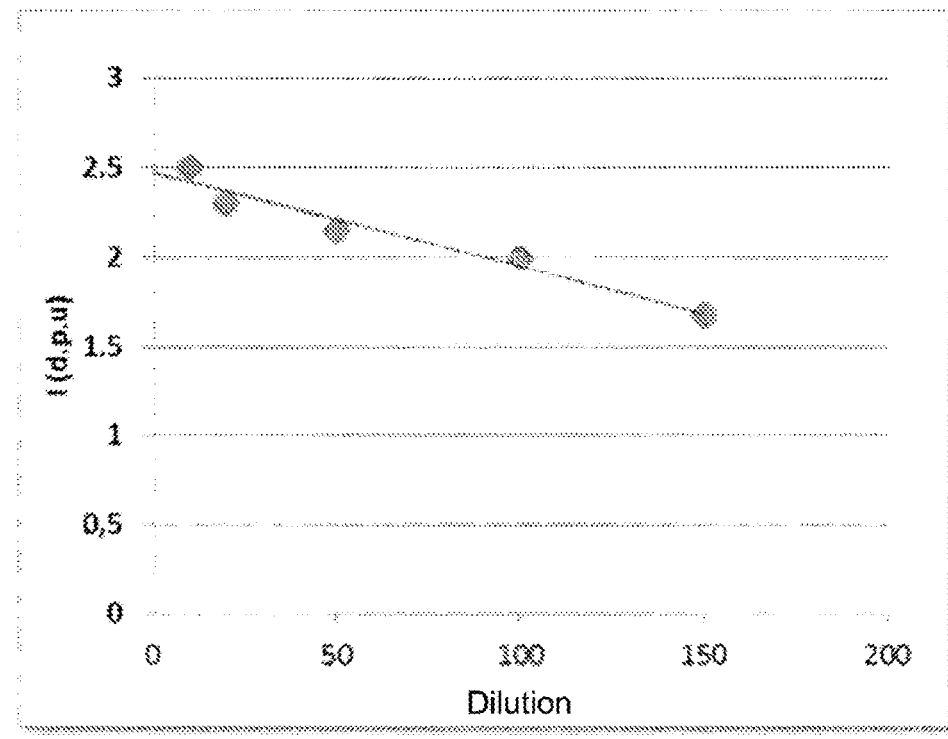
FIG. 2 shows the graph of signal intensity at the emission wavelength $\lambda_{em}$ as a function of the dilution of a stock solution of a polymer with a known anionic charge density.
Figure 3:
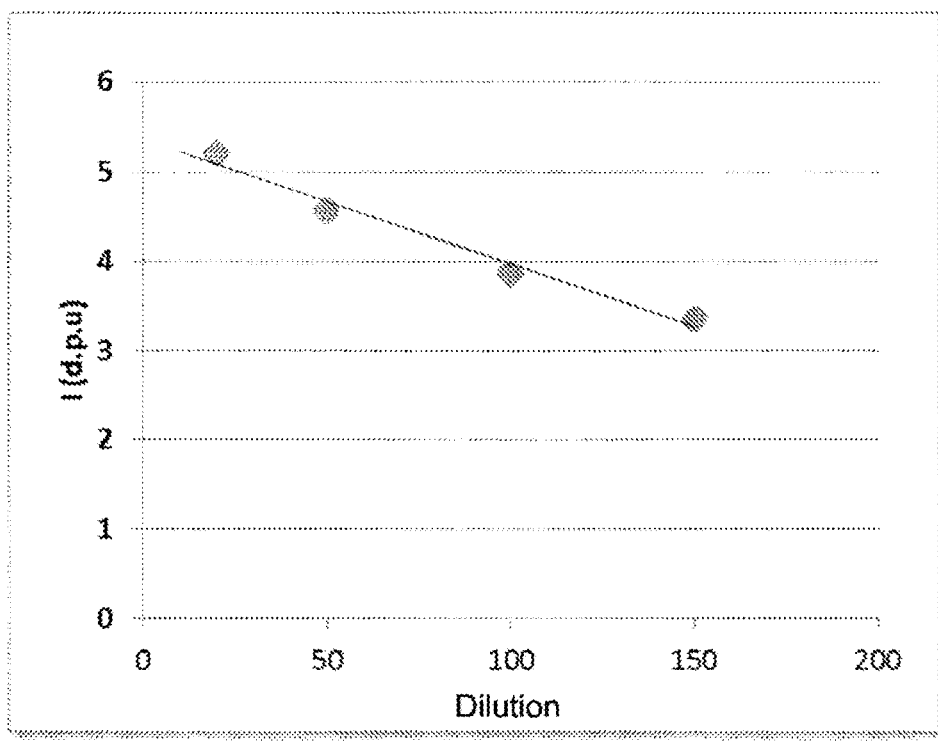
FIG. 3 shows the graph of signal intensity at the emission wavelength $\lambda_{em}$ as a function of the dilution of a stock solution of a polymer with a known anionic charge density.
Figure 4:
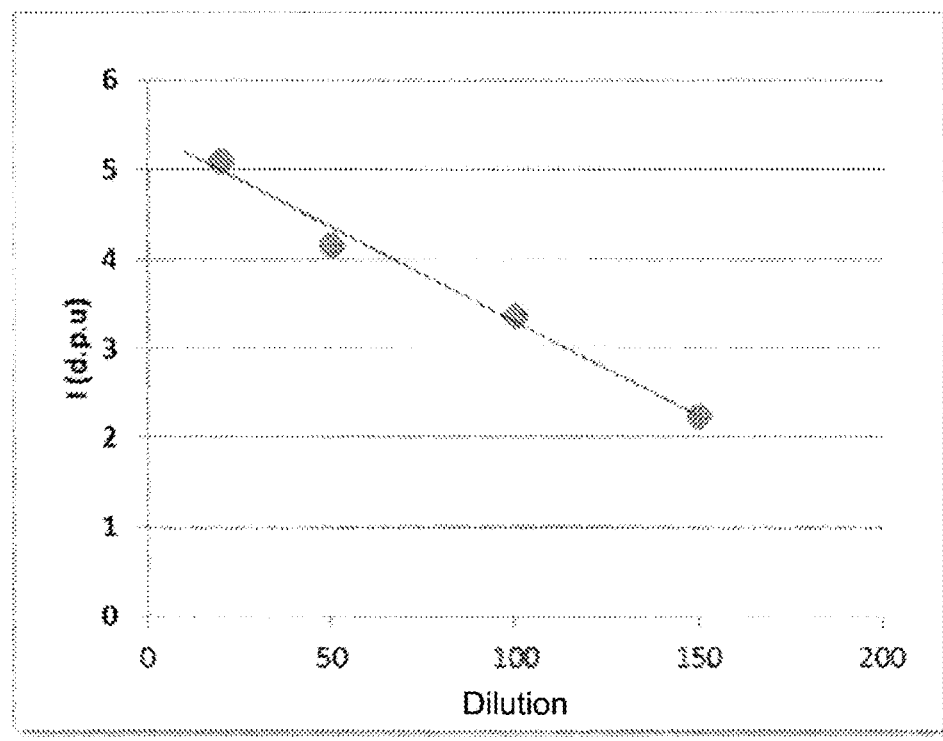
FIG. 4 shows the graph of signal intensity at the emission wavelength $\lambda_{em}$ as a function of the dilution of a stock solution of a polymer with a known anionic charge density.
Figure 5:
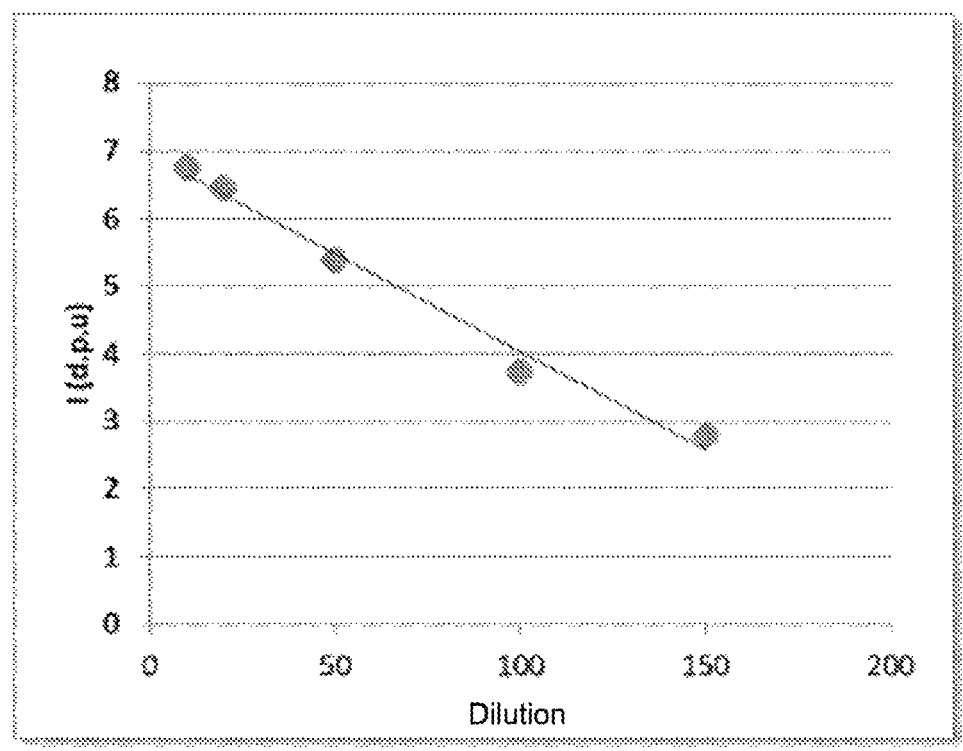
FIG. 5 shows the graph of signal intensity at the emission wavelength $\lambda_{em}$ as a function of the dilution of a stock solution of a polymer with a known anionic charge density.
Figure 6:
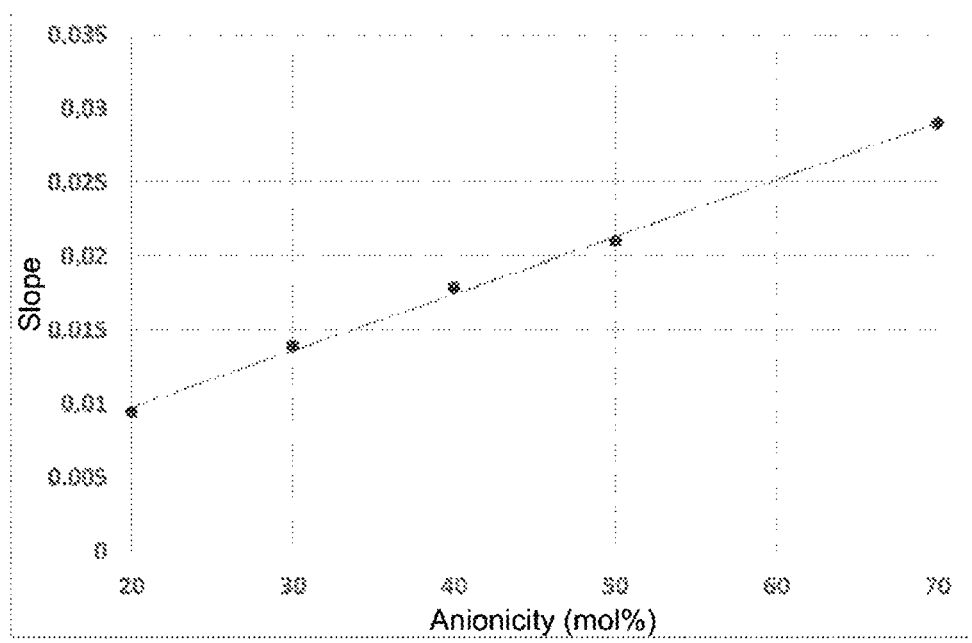
FIG. 6 shows the linear variation in the slope of each of FIGS. 1 to 5.

The excitation spectra of the various solutions in Table 1 are performed at $\lambda_{exc}$=320 nm and $\lambda_{em}$=545 nm.
Peak intensities as a function of dilution are shown in FIGS. 1 to 5.
FIG. 6 shows the linear variation in the slope of each of the curves in FIGS. 1 to 5.

e) Determination of the Anionicity of a Sample X of Polymer Diluted in Brine

A sample X of unknown anionicity was sampled from a volume of production water coming from oil production from reservoirs that use enhanced oil recovery techniques that inject a polymer-based solution.

Five solutions of various unknown concentrations are prepared by successively diluting the sample with brine (see paragraph a): 25.00 g·L$^{-1}$
NaCl and 1 g·L$^{-1}$ CaCl$_2$)).

Each of these 5 solutions is mixed (1 vol/10 vol) with a developer solution of Terbium III Chloride sold by Glincs. The pH is 6.5.

Figure 7:
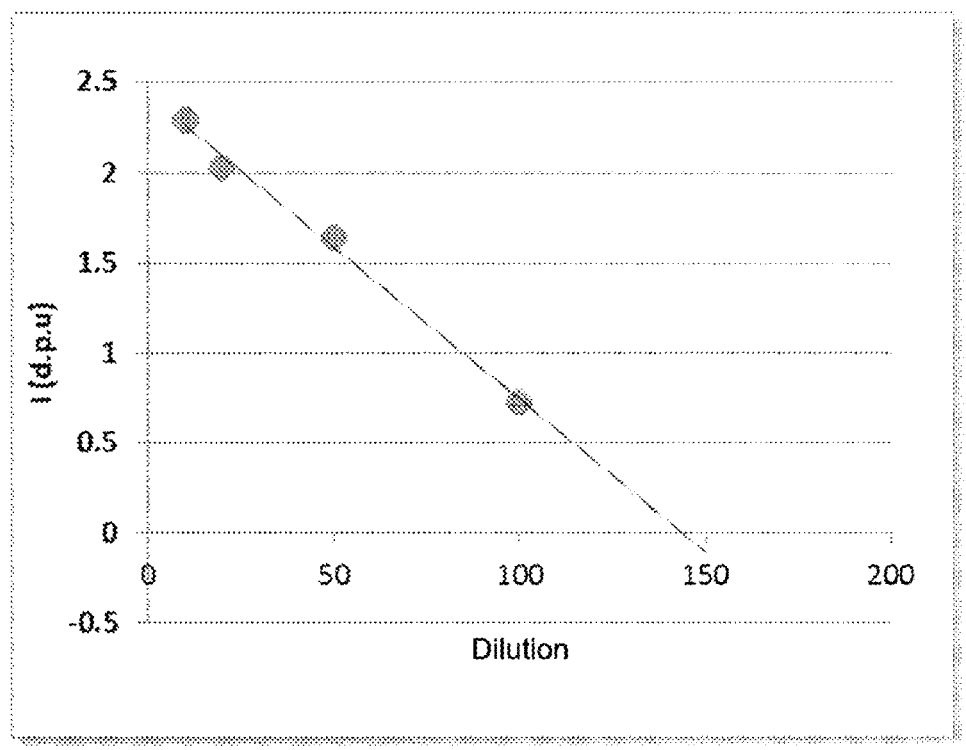
FIG. 7 shows the graph of signal intensity at the emission wavelength $\lambda_{em}$ as a function of the dilution of a stock solution of a polymer with an unknown anionic charge density.

The intensities obtained as a function of dilution are shown in FIG. 7.

After extrapolating the slope from the line in FIG. 7 and correlating it with the calibration line in FIG. 6, the anionicity of the polymer is deduced to be 39.25 mol %.

Example 2—Determining the Anionicity of a Polymer Present in a Drilling Fluid

This example concerns the determination of the anionicity of an anionic polymer of unknown composition present in drilling fluid collected at the outlet of producing oil wells.

a) Equipment & Measurements

Photoluminescence measurements are made at room temperature in a quartz cuvette on a spectrometer like the Cary Eclipse Fluorescence Spectrophotometer from Agilent. The characteristics are identical to those in Example 1.

The excitation spectra of the samples are performed between 200 and 450 nm and the emission wavelength $\lambda_{em}$ is 617 nm.

The measurement parameters are set as follows:
Time: 0.5 ms
Photon collection time: 2 ms
Lamp frequency: 100 Hz
Number of flashes: 1
The analysis is started using the software controlling the spectrofluorometer.

b) Preparation of Control Samples & Excitation Spectra

The following solutions of various unknown concentrations are prepared by successively diluting a polymer stock solution with water that has the same salinity as the drilling fluid to be analyzed (Table 2).

TABLE 2

Anionicity of control references F to I

| Polymer Reference | Anionicity (mol %) |
|---|---|
| F | 15 |
| G | 25 |
| H | 35 |
| I | 45 |

Each of the solutions listed in Table 2 is mixed (1 vol/10 vol) with a developer solution of Europium III chloride, sold by Glincs. The pH is 6.5.

Figure 8:
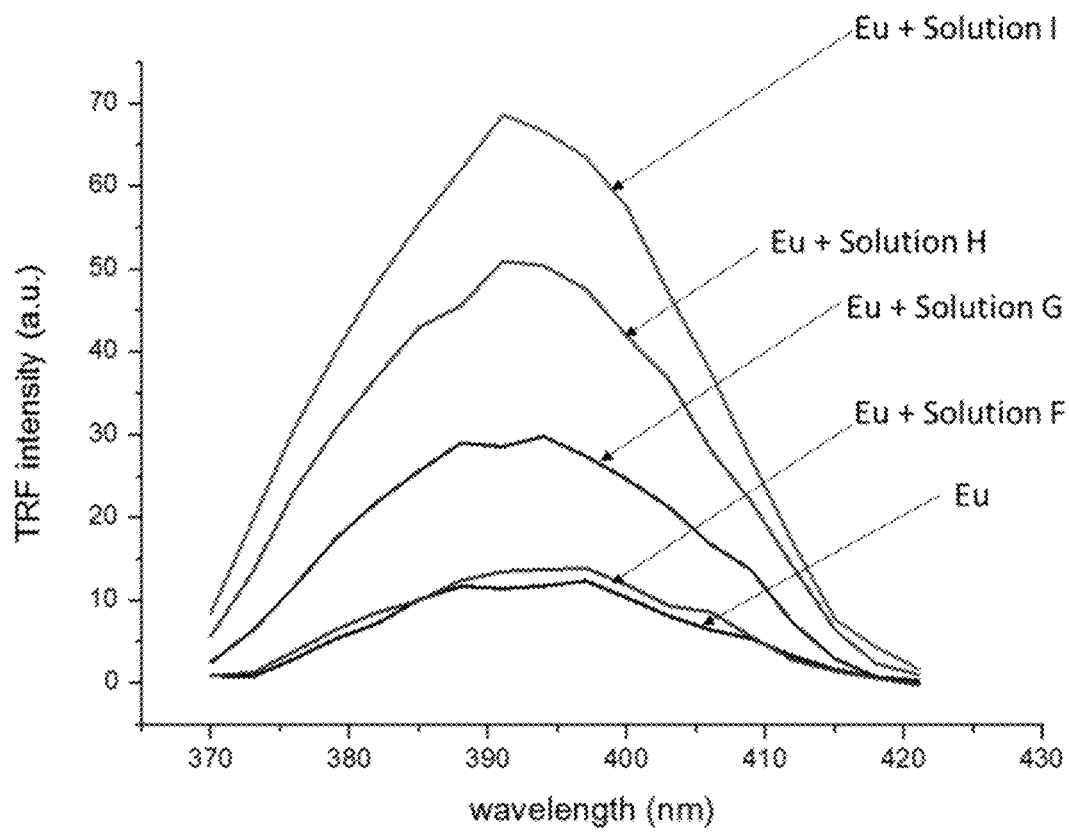
FIG. 8 represents the signal intensity as a function of the emission wavelength for polymers with a known anionic charge density.

FIG. 8 shows a change in the intensity of the peaks on the excitation spectrum, reflecting a complexing of the Europium ions with the study solutions.

c) Determination of the Anionicity of Control Samples

The excitation spectra of the various solutions in Table 2 are performed at $\lambda_{exc}$=395 nm and $\lambda_{em}$=617 nm.

Figure 9:
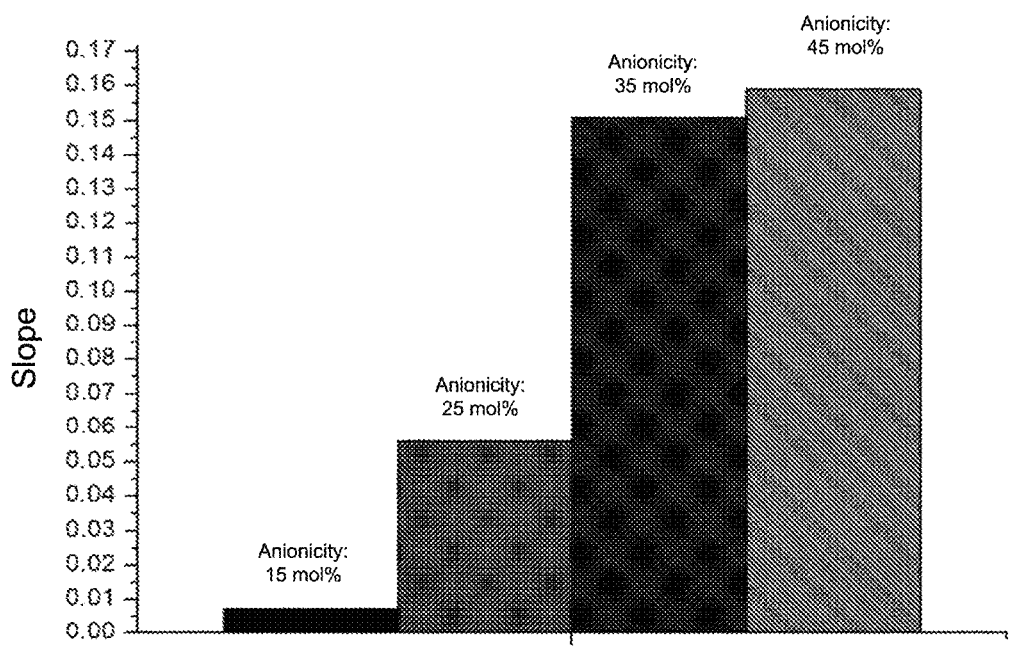
FIG. 9 represents the slope (intensity as a function of dilution) as a function of the anionicity for polymers with a known anionic charge density.

FIG. 9 shows the slopes obtained as a function of the anionicities of the controls.

d) Determination of the Unknown Anionicity of the Drilling Fluid Sample

A sample of unknown anionicity was taken from the drilling fluid. It was filtered to remove insoluble substances. Solutions of various (unknown) concentrations are prepared by successively diluting the sample with water that has the same salinity as the drilling fluid to be analyzed. The 5 solutions are mixed (1 vol/10 vol) with a developer solution of Europium III Chloride, sold by Glincs. The pH is 6.5.

The slope resulting from the linear variation in the intensity of the fluorescence peaks obtained as a function of dilution is 0.152. After correlation with the calibration line in FIG. 9, the anionicity of the polymer is deduced to be 36.17 mol %.

Example 3—Improving the Sensitivity of the Anionicity Determination of a Copolymer This example concerns the use of operating conditions to improve the sensitivity and resolution of the anionicity determination measurement of an acrylamide/sodium acrylate copolymer present, for example, in petroleum production water from reservoirs that use enhanced polymer-based oil recovery techniques or in a drilling fluid.

a) Time-Resolved Luminescence Measurement

Measurements are made at 20° C. in a quartz cuvette on a spectrometer like the Cary Eclipse Fluorescence Spectrophotometer from Agilent with the following characteristics:
  75 kW Xenon flash lamp
  Czerny-Turner monochromators
  PM detector at 800 V
  Δpulse=2 μs The excitation spectra of the samples are performed between 200 and 450 nm. The emission wavelength is $\lambda_{em}$=617 nm.

The measurement parameters are set as follows:
  Time: 0.5 ms
  Photon collection time: 2 ms
  Lamp frequency: 100 Hz
  Number of flashes: 1

The analysis is started using the software controlling the spectrofluorometer.

b) Preparation of Control Solutions and Determination of Anionicity

Solutions of various unknown concentrations are prepared by successively diluting a polymer stock solution with brine ([NaCl]=150 g/L) (Table 3).

The excitation spectra of these various solutions are performed at $\lambda_{exc}$ 395 nm and $\lambda_{em}$=617 nm. Each of the solutions listed in Table 1 is mixed with a developer solution of Europium III, sold by Glincs. The pH is 6.5.

TABLE 3

Anionicity of control polymers R1 to R4
Polymer

| Reference | Anionicity (mol %) |
|---|---|
| R1 | 15 |
| R2 | 25 |
| R3 | 35 |
| R4 | 45 |

Figure 10:
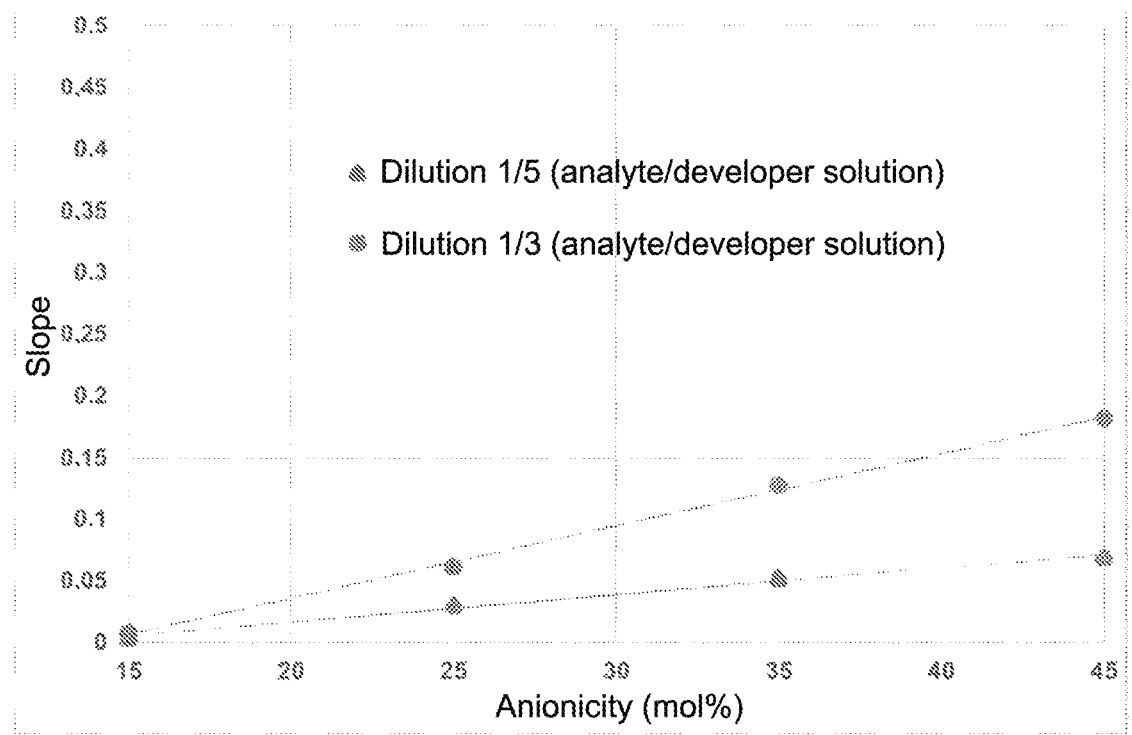
FIG. 10 shows the variations in slope as a function of anionicity at different dilution rates.

Slope variations as a function of anionicity at different dilution rates (Analyte)/(Developer Solution) were obtained (FIG. 10).

A sample of unknown anionicity was taken from a drilling fluid. It was filtered to remove insoluble substances. Five solutions of various (unknown) concentrations are prepared by successively diluting the sample with brine. Each of these 5 solutions is mixed (1 vol/3 vol) with a developer solution of Europium III sold by Glincs. The pH is 6.5. The slope resulting from the linear variation in the intensity of the fluorescence peaks obtained as a function of dilution is 0.095. After correlation with the calibration line in FIG. 10, the anionicity of the polymer is deduced to be 30 mol %.

This example once again demonstrates that the anionicity of a polymer can be determined using the time-resolved fluorescence technique and that the sensitivity of the measurement can be improved by working in a medium with a higher salt concentration.

The invention claimed is:

1. A method for determining the anionic charge density of at least one polymer present in a sample, the method comprising the following steps:
  bringing the at least one polymer present in the sample into contact with a developer solution comprising lanthanide (III) ions, and enabling interactions between the at least one polymer and the lanthanide (III) ions,
  exciting the sample at an excitation wavelength of $\lambda_{exc}$ and detecting, by time-resolved photoluminescence, a signal originating from the lanthanide (III) ions that have interacted with the at least one polymer at an emission wavelength $\lambda_{em}$, and
  determining the anionic charge density of the at least one polymer in the sample using the signal detected at the emission wavelength $\lambda_{em}$ according to the following protocol:
    1) different sample series are prepared by successively diluting various stock solutions of polymers of known anionic charge density with water, samples from each series are then diluted with the developer solution comprising the lanthanide (III) ions and analyzed by Time-Resolved Fluorescence (TRF); measurement parameters as well as the emission and excitation wavelengths are adjusted according to a type of lanthanide,
    2) for each series, slopes of TRF Signal Intensity vs. Dilution Rate curves are extrapolated and a Slope vs. Anionic Charge Density calibration curve is developed,
    3) a new series of samples is then prepared by successively diluting a sample X of unknown anionic charge density, after TRF measurement of these samples, the slope of the TRF Signal Intensity vs Dilution Rate curve is extrapolated,
    4) after the extrapolated slope in 3) is correlated with the Anionic Charge Density calibration curve developed in step 2), the previously unknown anionic charge density of the sample X is deduced.

2. The method according to claim 1, wherein the sample having the at least one polymer present comes from production water from an oil or gas recovery process.

3. The method according to claim 1, wherein the time-resolved photoluminescence is time-resolved fluorescence.

4. The method according to claim 3, wherein the at least one polymer present in the sample is a polymer of at least one water-soluble anionic monomer and at least one non-ionic monomer (A) and, optionally, of at least one cationic or zwitterionic monomer.

5. The method according to claim 1, wherein the at least one polymer present in the sample is a polymer of at least one water-soluble anionic monomer and at least one non-ionic monomer (A) and, optionally, of at least one cationic or zwitterionic monomer.

6. The method according to claim 5, wherein the lanthanide (III) ions are chosen from europium, terbium, samarium and dysprosium ions.

7. The method according to claim 5, wherein the lanthanide (III) ions are europium or terbium ions.

8. The method according to claim 5, wherein the excitation wavelength $\lambda_{exc}$ lies between 200 nm and 600 nm and the emission signal wavelength $\lambda_{em}$ lies between 300 nm and 800 nm.

9. The method according to claim 5, wherein between 1 ppm and 10,000 ppm of the lanthanide (III) ions is added to the sample having the at least one polymer present by weight based on the weight of the sample having the at least one polymer present before the sample having the at least one polymer present comes into contact with the developer solution.

10. The method according to claim 9, wherein the excitation wavelength $\lambda_{exc}$ lies between 200 nm and 600 nm and the emission signal wavelength $\lambda_{em}$ lies between 300 nm and 800 nm.

11. The method according to claim 5, wherein the method comprises a sample purification step prior to adding the developer solution comprising the lanthanide (III) ions.

12. The method according to claim 5, wherein a signal modifier comprising a cationic compound is added to the sample having the at least one polymer present before the sample having the at least one polymer present is excited.

13. The method according to claim 12, wherein the method comprises a sample purification step prior to adding the developer solution comprising the lanthanide (III) ions.

14. The method according to claim 1, wherein the lanthanide (III) ions are chosen from europium, terbium, samarium and dysprosium ions.

15. The method according to claim 1, wherein the lanthanide (III) ions are europium or terbium ions.

16. The method according to claim 1, wherein between 1 ppm and 10,000 ppm of the lanthanide (III) ions is added to the sample having the at least one polymer present by weight based on the weight of the sample having the at least one polymer present before the sample having the at least one polymer present comes into contact with the developer solution.

17. The method according to claim 1, wherein the excitation wavelength $\lambda_{exc}$ lies between 200 nm and 600 nm and the emission signal wavelength $\lambda_{em}$ lies between 300 nm and 800 nm.

18. The method according to claim 1, wherein a signal modifier comprising a cationic compound is added to the sample having the at least one polymer present before the sample having the at least one polymer present is excited.

19. The method according to claim 1, wherein the method comprises a sample purification step prior to adding the developer solution comprising the lanthanide (III) ions.

20. The method according to claim 19, wherein between 1 ppm and 10,000 ppm of the lanthanide (III) ions is added to the sample having the at least one polymer present by weight based on the weight of the sample having the at least one polymer present before the sample having the at least one polymer present comes into contact with the developer solution.

* * * * *